United States Patent [19]

Hartman et al.

[11] Patent Number: 4,721,708

[45] Date of Patent: Jan. 26, 1988

[54] CYCLIZED N-SUBSTITUTED-TETRAHYDROPYRIDINE COMPOUNDS AND CARDIOVASCULAR USE

[75] Inventors: George D. Hartman, Lansdale; Brian T. Phillips, Telford, both of Pa.

[73] Assignee: Merck & Co., Inc., Rahway, N.J.

[21] Appl. No.: 802,128

[22] Filed: Nov. 26, 1985

[51] Int. Cl.$^4$ .................. C07D 471/06; A61K 31/55; A61K 31/455

[52] U.S. Cl. .................... 514/214; 514/306; 540/593; 546/138; 546/321

[58] Field of Search ............. 546/138, 321; 514/306, 514/214; 540/593

[56] References Cited

U.S. PATENT DOCUMENTS

| | | | |
|---|---|---|---|
| 3,883,543 | 5/1975 | Bossert | 546/321 |
| 3,905,970 | 9/1975 | Bossert et al. | 546/321 |
| 3,923,818 | 12/1975 | Bossert et al. | 546/321 |
| 4,044,141 | 8/1977 | Bossert et al. | 546/321 |
| 4,237,137 | 12/1986 | Tacke et al. | 546/14 |
| 4,285,955 | 8/1981 | Wehinger et al. | 546/321 |

OTHER PUBLICATIONS

Weller, D. D. et al., J. Org. Chem. (1983), 48, pp. 3061–3067.

Goldmann, S., Angew. Chem. Int. Ed. Engl., 20 (1981), pp. 779–780.

*Primary Examiner*—Henry R. Jiles
*Assistant Examiner*—Dale A. Bjorkman
*Attorney, Agent, or Firm*—Alice O. Robertson; Michael C. Sudol

[57] ABSTRACT

Novel N-substituted tetrahydropyridine compounds are disclosed. The compounds have the property of inhibiting calcium induced contraction of smooth muscle and are adaptable to being employed in the chemotherapeutic treatment of cardiovascular diseases.

7 Claims, No Drawings

CYCLIZED N-SUBSTITUTED-TETRAHYDROPYRIDINE COMPOUNDS AND CARDIOVASCULAR USE

DESCRIPTION OF THE INVENTION

The present invention is directed to novel N-substituted tetrahydropyridine compounds cyclized through the dihydropyridine nitrogen and represented by the formula:

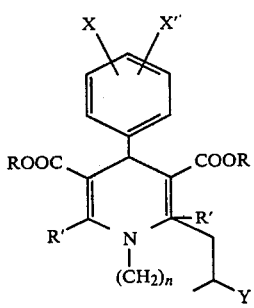

In this and succeeding formulas,

X and X' are independently hydrogen, halogen, lower alkyl, lower alkoxy, nitro or trifluoromethyl;

R is lower alkyl;

R' is lower alkyl;

Y is halogen, alkenoyloxy or alkylsulfonyloxy and n is 2 or 3, and pharmaceutically acceptable salts thereof.

The expressions "lower alkyl" and "lower alkoxy" refer to radicals having from 1 to 6 carbon atoms, inclusive. The expression "halogen" refers to fluorine, chlorine and bromine.

The compounds can exist in diastereomeric forms. All diasteromeric forms are included within the scope of the present invention.

The preferred compounds are those in which n is 2 and Y is halogen which may be represented by the formula:

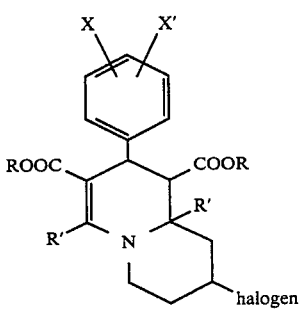

The most preferred compounds are those compounds which may be represented by the formula

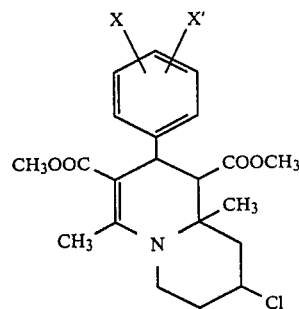

The compounds of the present invention are generally white crystalline solids, soluble in most organic solvents. Some of the products may crystallize as hydrates.

The tetrahydro pyridine nitrogen in the compounds is basic and forms salts. The pharmaceutically acceptable salts within the scope of the present invention are acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic and trichloroacetic and the like and include acids related to the pharmaceutically acceptable salts listed in Journal of Pharmaceutical Science, 66, 2 (1977) and incorporated herein by reference.

The compounds have shown pharmacological properties which would render them useful as calcium entry blockers. The compounds of the present invention are structurally quite different from other calcium entry blockers in that the nitrogen of the tetrahydropyridine is substituted and furthermore is part of the bridge of a condensed ring system. The properties render the compounds adaptable for application in the chemotherapeutic treatment of cardiovascular disorders caused by high cellular concentration of $Ca^{++}$. The compositions containing these compounds and methods for using the compounds in the treatment of cardiovascular disorders constitute an aspect of the present invention.

The compounds of Formula I may be prepared by cyclizing an appropriate dihydropyridine compound represented by Formula II:

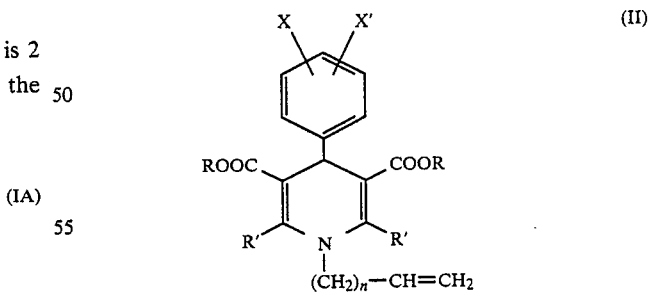

with an acid catalyst in an inert solvent under an inert atmosphere.

The starting dihydropyridine compound of Formula II may be prepared by reacting an appropriately substituted aminoalkenoate compound,

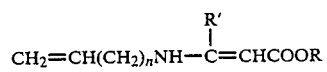

with an appropriate benzaldehyde compound

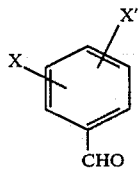

by a procedure as hereinafter described and which is an application of a method described and claimed in co-pending application Ser. No. 828,474 of Steven M. Pitzenberger et al.

The agent for the cyclization reaction to form the compound of Formula I is an acid which is employed in molar excess, from about 1.5 to 3.5 molar excess. The acid may be a conventional proton donor (Bronsted acid) or a Lewis acid. The term "Lewis acid" is meant to refer to compounds understood by the skilled artisan as reagents having either an empty or potentially empty orbital which can accept an electron pair or lose a group with an electron pair in the course of a reaction. Suitable acids include titanium tetrachloride, gaseous hydrogen chloride, gaseous hydrogen bromide, zinc iodide, zinc chloride, boron trifluoride, trimethylsilyl trifluoromethane sulfonate, aluminum chloride and the like. Titanium tetrachloride is especially preferred.

The reaction is carried out in an inert solvent as reaction medium. Suitable solvents include halogenated hydrocarbons such as chloroform, carbon tetrachloride, methylene dichloride, ethylene dichloride, and hydrocarbon solvents such as benzene, toluene and the like.

The inert atmosphere is generally provided by nitrogen although other inert gases such as argon and the like, also may be employed.

The reaction is generally carried out at ambient temperature for the time sufficient for completion of the reaction. Usually from about 1 to 18 hours are employed.

In carrying out the reaction according to a preferred method, titanium tetrachloride is added with stirring at ambient temperature to a solution of the dihydropyridine compound (II) in an inert organic solvent in an inert atmosphere, and the stirring continued for time sufficient to substantially complete the reaction. At this time, the water is added to the reaction mixture and then a sodium bicarbonate solution to neutralize the mixture. The resulting mixture is extracted with organic solvent to recover the product in the organic solution. The product is obtained from the organic solution first washing and drying the organic solution and thereafter vaporizing the solvent and recovering the product of Formula I as residue. The product may be purified by flash chromatography (J. Org. Chem. 43, 2923 (1978)) on silica gel using hydrocarbon/ether eluant to obtain a purified product. If desired, the product may be further purified by recrystallization.

The compounds of the present invention have a property rendering them adaptable for use as calcium entry blockers in the treatment of cardiovascular disorders. The usefulness of the compounds as calcium entry blockers may be demonstrated in a nitrendipine binding assay wherein effective inhibition of nitrendipine binding is indicative of effectiveness as a calcium entry blocker.

In a representative assay, 20 μg of purified sarcolemnal vesicles in 50 mM tris-HCl, 10 μM calcium chloride, and 10 μM magnesium chloride, at pH 7.4 are incubated with 0.23 mM [³H] nitrendipine 78 Ci/mmol) with or without test compound in a final volume of 200 μl for 3 hours at 25° C. The inhibition constant $K_i$ is determined according to the following equation $$K_i = \frac{I_{50}}{1 + \frac{[L]}{k_d}}$$

where $I_{50}$ is concentration that produces 50 percent inhibition of binding, [L] is ligand concentration, and $K_d$ is the affinity constant of the ligand. When dimethyl 8-chloro-1,6,7,8,9,9a-dimethyl-2-phenyl-2H-quinolizine-1,3-dicarboxylate was employed as the test compound, effective inhibition of nitrendipine binding was observed at concentrations as low as about $10^{-4}$M.

Effective nitrendipine binding indicates usefulness of the compounds in the study and treatment of cardiovascular diseases.

For use in the chemotherapeutic treatment of cardiovascular diseases, an effective amount of the compounds of the present invention may be administered orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration. The dosage level for the compounds may be varied from about 0.05 milligram to about 7.0 milligrams per kilogram of body weight per day. Daily doses in the range of 1 to 3.5 mg/kg are preferred. These doses are suitable for any of the utilities described herein.

The compound may be formulated with a pharmaceutical carrier or diluent.

To prepare the pharmaceutical compositions of this invention, a compound of Formula (I) is intimately admixed with a pharmaceutical carrier according to conventional pharmaceutical compounding techniques, which carrier may take a wide variety of forms depending on the form of preparation desired for administration, e.g., oral or parenteral.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques.

For parenterals, the carrier will usually comprise sterile water, although other ingredients may be included, for such purposes as aiding solubility or preservation. Injectable suspensions also may be prepared, in which case appropriate liquid carriers, suspending agents and the like may be employed.

The concentration of the compound of Formula I in the compositions of the present invention may vary depending on whether the composition is intended for direct application or for subsequent dilution. If intended to be concentrate compositions from 2 to 95 percent active ingredient may be present. If for ultimate therapeutic application the compositions will contain, per dosage unit, e.g., tablet, capsule, powder, injection, teaspoonful and the like, from about 10 to about 1000 mg of the active ingredient, preferably, from about 10 to about 250 mg.

The following examples illustrate the invention but are not to be construed as limiting.

EXAMPLE 1

Dimethyl 8β-Chloro-1,6,7,8,9,9a-hexahydro-4,9aα-dimethyl-2-phenyl-2H-quinolizine-1β,3-dicarboxylate

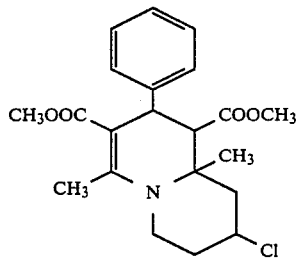

Step A: Methyl 3-N-(1-buten-4-yl)aminocrotonate 2.15 milliliters (2.32 grams, 20.0 millimoles) of methyl acetoacetate was added with stirring to 1.42 grams (20.0 millimoles) of homoallyl amine cooled in an ice bath and the stirring continued while the mixture was allowed to warm to room temperature and thereafter for three hours to obtain a methyl 2-N-(1-buten-4-yl)aminocrotonate intermediate product and water by-product in the reaction mixture. 20 milliliters of diethyl ether was added to dissolve the intermediate ester product and the ether solution separated from the aqueous layer. The ether solution was washed with brine, then dried over sodium sulfate, the dried solution purified by passing through a silica gel pad, and the purified solution subjected to reduced pressure to remove the solvent and to recover 3.35 grams of methyl 3-N-(1-buten-4-yl)aminocrotonate as an oil.

Step B: Dimethyl 1-(1buten-4yl)-2,6-dimethyl-4-phenyl-1,4-dihydropyridine-3,5-dicarboxylate To a solution of 0.80 gram (4.2 millimoles) of titanium tetrachloride in 17 milliliters of benzene under an atmosphere of nitrogen, was added dropwise with rapid stirring, 0.72 gram (8.5 millimoles) of piperidine whereupon a green mixture was produced. To this mixture was added dropwise, a freshly prepared solution of 2.88 grams (17 millimoles) of methyl 3-N-(1-buten-4-yl)aminocrotonate in 4 milliliters of benzene whereupon a reaction took place with the formation of a dark purple mixture. The mixture was stirred for an additional 5 minutes and then to it was added dropwise a solution of 0.90 gram (8.5 millimoles) of benzaldehyde in 4 milliliters of benzene. The resulting mixture was initially viscous but became more fluid as the stirring was continued and formed a yellow solution and a gummy brown precipitate. Stirring was continued for three hours at which time the reaction was quenched by adding 35 milliliters of 3N hydrochloric acid. The mixture was extracted with three 100 milliliter portions of diethyl ether and the ether extract washed successively with 3N-hydrochloric acid, saturated aqueous sodium bicarbonate and brine, and then dried over sodium sulfate. The solvent was vaporized from the dried solution under reduced pressure to obtain a yellow oil which when triturated with ether produced a white solid of dimethyl 1-(1-buten-4-yl)-2,6-dimethyl-4-phenyl-1,4-dihydropyridine-3,5-dicarboxylate intermediate, m.p. 108°–110° C. and $R_f$ 0.4 on silica gel when eluted with 2:1 hexane/ether.

Step C: Dimethyl 8β-chloro-1,6,7,8,9,9a-hexahydro-4,9aα-dimethyl-2-phenyl-2H-quinolizine 1β,3-dicarboxylate 0.076 gram (0.4 millimole) of titanium tetrachloride was added under an atmosphere of nitrogen to a solution of 0.07 gram (0.4 millimole) of dimethyl 1-(1-buten-4-yl)-2,6-dimethyl-4-phenyl-1,4-dihydropyridine-3,5-dicarboxylate in 2 milliliters of chloroform and the resulting mixture stirred for 48 hours. At the end of this period, the reaction was quenched with water, neutralized with saturated sodium bicarbonate solution and extracted with three 5 milliliter portions of chloroform. The extracts were combined and the combined extracts washed with brine and dried over sodium sulfate. The solvent was then stripped under reduced pressure and a yellow oil recovered as residue. The latter was purified by flash chromatography on silica gel eluting with 3:1 hexane/ether to obtain a residue which on triturating with ether produced the desired dimethyl 8β-chloro-1,6,7,8,9,9a-hexahydro-4,9aα-dimethyl-2-phenyl-2H-quinolizine-1β,3-dicarboxylate product, m.p. 151°–153° C.

EXAMPLE 2

Diethyl 8β-chloro-1,6,7,8,9,9a-hexahydro-4,9aα-dimethyl-2-(4-trifluoromethylphenyl)-2H-quinolizine-1β,3-dicarboxylate

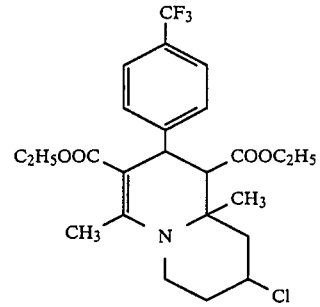

In a manner similar to that described in Example I, 2.6 grams (20 millimoles) of ethyl acetoacetate is added with stirring to 1.42 grams (20 millimoles) of homoallyl amine cooled in an ice bath and the stirring continued with gradual warming to ambient temperature to obtain an ethyl 3-N-(1-buten-4-yl)aminocrotonate intermediate in the reaction mixture. The intermediate is recovered from the mixture by dissolving in diethyl ether thereafter washing and drying the ether solution and then removing the solvent in a manner previously described to recover the ester product.

A solution of 1.69 grams (10 millimoles) of the ester in 5 milliliters of benzene is added dropwise with rapid stirring under an atmosphere of nitrogen to a solution of 0.32 gram (4.3 millimoles) of piperidine and 0.4 gram (2.1 millimole) of titanium tetra chloride in 10 milliliters of benzene and the stirring continued until reaction subsides. Then a solution of 0.75 gram (4.3 millimoles) of 4-trifluorm nethylbenzaldehyde in 5 milliliters of benzene is added and the stirring continued for several hours with the formation of a diethyl 1-(1-buten-4-yl)-2,6-dimethyl-4-(4-trifluoromethylphenyl)-1,4-dihydropyridine-3,5-dicarboxylate product in the reaction mixture. Thereafter, the reaction is quenched by the addition of dilute hydrochloric acid. The product is then recovered as described in Example 1.

0.19 gram (1 millimole) of titanium tetrachloride is added under an atmosphere of nitrogen to a solution of 0.45 gram (1 millimole) of the diethyl 1-(1-buten-4-yl)-2,6-dimethyl-4-(4-trifluoromethylphenyl)-1,4-dihydropyridine-3,5-dicarboxylate product in 15 milliliters of chloroform and the resulting mixture stirred overnight to obtain a diethyl 8β-chloro-1,6,7,8,9,9aα-hexahydro-4,9aα-dimethyl-2-(4-trifluoromethylphenyl)-2H-quinolizine-1β,3-dicarboxylate product in the reaction mixture. The reaction mixture is quenched with water and the product recovered as residue in a manner similar to that described in Example 1.

EXAMPLE 3

Di(n-hexyl) 8β-chloro-1,6,7,8,9,9a-hexahydro-4,9aα-dimethyl-2-(3-nitrophenyl)-2H-quinolizine-1β,3-dicarboxylate

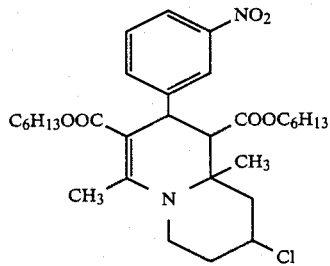

In a manner similar to that described in the preceding examples, n-hexyl 3-(N-buten-4-yl))aminocrotonate is prepared from n-hexyl acetoacetate and homoallylamine by mixing the reactants and causing them to react first with cooling and thereafter at ambient temperature. The ester thus prepared is recovered from the reaction mixture employing conventional procedures. A benzene solution of the ester then is added dropwise with stirring under an atmosphere of nitrogen to a solution complex of titanium tetrachloride in piperidine, followed by a benzene solution of 3-nitrobenzaldehyde to obtain a di(n-hexyl) 1-(1-buten-4-yl)-2,6-dimethyl-4-(3-nitrophenyl)-1,4-dihydropyridine-3,5-dicarboxylate ester product. The dihydropyridine dicarboxylate ester then is cyclized by adding titanium tetrachloride to obtain the desired di(n-hexyl) 8β-chloro-1,6,7,8,9,9aα-hexahydro-4,9a-dimethyl-2-(3-nitrophenyl)-2H-quinolizine-1β,3-dicarboxylate product in the reaction mixture is quenched with water and the product recovered as residue in a manner similar to Example 1.

EXAMPLE 4

In similar operations, the compounds in the following table may be prepared from the appropriate starting material by cyclization with titanium tetrachloride or hydrogen bromide in an inert solvent under an atmosphere of nitrogen.

| Compound | R | R' | X | X' | Y | n |
|---|---|---|---|---|---|---|
| IV | $CH_3$ | $C_5H_{11}$ | 4-$CH_3O$ | H | Br | 2 |
| V | i-$C_3H_7$ | $CH_3$ | 4-Br | H | Br | 2 |
| VI | n-$C_4H_9$ | $CH_3$ | 4-t-$C_4H_9$ | H | Br | 2 |
| VII | $CH_3$ | n-$C_4H_9$ | 3-$NO_2$ | 4-$CH_3$ | Cl | 2 |
| VIII | $CH_3$ | $CH_3$ | 4-$CF_3$ | H | $SO_3CH_3$ | 3 |
| IX | $C_2H_5$ | $CH_3$ | 4-$C_4H_9O$ | 2-Br | $OCOCH_3$ | 3 |
| X | n-$C_4H_9$ | $CH_3$ | 3-$NO_2$ | 5-$C_2H_5$ | Cl | 3 |

EXAMPLE 5

10,000 hard gelatin capsules each containing as active ingredient 25 milligrams of dimethyl 8β-chloro-1,6,7,8,9,9a-hexahydro-4,9aα-dimethyl-2-phenyl-2H-quinolizine-1β,3-dicarboxylate are prepared from the following formulation:

|  | Grams |
|---|---|
| Active ingredient | 250 |
| Lactose | 750 |
| Starch | 250 |
| Talc | 250 |
| Calcium stearate | 10 |

A uniform mixture of the active and supplementary ingredients is prepared and filled into two-piece hard gelatin capsules. The capsules are suitable for oral administration to provide therapeutic relief for patients with cardiovascular disorders.

EXAMPLE 6

Capsules are made by substituting for the active compound of Example 5 one of the following:
(1) diethyl 8β-chloro-1,6,7,8,9,9a-hexahydro-4,9aα-dimethyl-2-(4-triflurometylphenyl)-2H-quinolizine-1β,3-dicarboxylate;
(2) di-(n-hexyl) 8β-chloro-1,6,7,8,9,9a-hexahydro-4,9aα-dimethyl-2-(nitrophenyl)-2H-quinolizine-1β,3-dicarboxylate;
(3) dimethyl 8β-bromo-1,6,7,8,9,9a-hexahydro-4,9aα-di(n-pentyl)-2-(4-methoxyphenyl)-2H-quinolizine 1β,3-dicarboxylate;
(4) dimethyl 8β-chloro-1,6,7,8,9,9a-hexahydro-4,9aα-dimethyl-2-phenyl-2H-quinolizine-1β,3-dicarboxylate hydrochloride;
(5) diethyl 8α-chloro[,]1,6,7,8,9,9a-hexahydro-4,9aα-dimethyl-2-(4-trifluoromethylphenyl)-2H-quinolizine-1β,3-dicarboxylate hydrogen maleate.

EXAMPLE 7

5,000 compressed tablets, each containing as active ingredient 10 milligrams of dimethyl 8β-chloro-1,6,7,8,9,9aα-hexahydro-4,9a-dimethyl-2-phenyl-2H-quinolizine-1β,3-dicarboxylate are prepared from the following formulation:

|  | Grams |
| --- | --- |
| Active ingredient | 50 |
| Starch | 70 |
| Dibasic calcium phosphate hydrous | 500 |
| Calcium stearate | 2.5 |

The ingredients are finely powdered, mixed well, and then granulated with 10 percent starch paste. The granulation is dried and compressed into tablets using starch as a disintegrant and calcium stearate as lubricant.

PREPARATION OF THE STARTING MATERIALS

The starting dihydropyridine compounds for preparing the compounds of the present invention may be prepared employing the reaction sequence depicted below or through a portion thereof depending on the availability of the precursor compounds. The preparation employs a process disclosed and claimed in the aforementioned application of Steven M. Pitzenberger, et al.

$$R'CH_2COCH_2COOR + CH_2=CH(CH_2)_nNH_2 \longrightarrow$$
(A) (B)

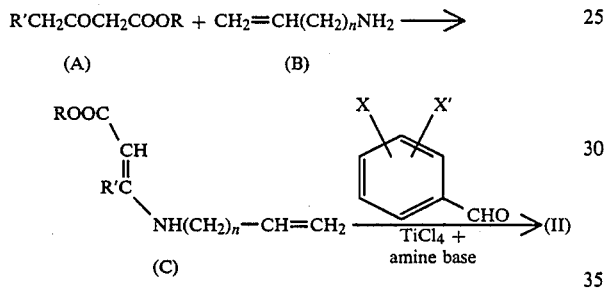

In carrying out the first step of the reaction, the appropriate aminoalkenyl compound (B) is added dropwise at ambient temperature to a stirred solution of alkyl acylacetate (A) and the stirring continued for time sufficient to obtain an alkyl 3-alkenylamino-2-alkenoate (C). The ester is recovered by dissolving in an ethereal solvent, conveniently, diethyl ether, then washing the other solution, drying the washed ether solution, and vaporizing the solvent to leave the ester as residue.

In carrying out the second step of the reaction, a benzene solution of titanium tetrachloride is prepared under nitrogen atmosphere and a nitrogen base such as piperidine is added thereto. To the resulting solution is added dropwise the ester compound (C) and the appropriate benzaldehyde compound

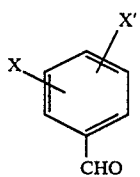

whereupon a reaction takes place with the formation of an N-substituted-1,4-dihydropyridine compound (II). The latter is recovered from the mixture employing conventional procedures.

The dihydropyridine compounds thus obtained are novel and useful not only as starting materials for the cyclized N-substituted tetrahydropyridine compounds of the present invention but are also useful as calcium entry blockers, having the property of inhibiting nitrendipine binding. Thus, for example, dimethyl 1-(1-buten-4-yl)-2,6-dimethyl-4-phenyl-1,4-dihydropyridine-3,5-dicarboxylate exhibits effective inhibition at $10^{-6}$M. These dihydropyridine compounds also have a basic nitrogen and therefore form salts. The intermediate dihydropyridine compounds and the pharmaceutically acceptable salts thereof constitute an aspect of the present invention.

What is claimed is:

1. A compound having the formula:

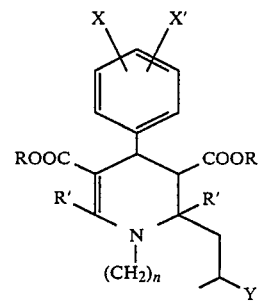

wherein
X and X' are independently hydrogen, halogen, lower alkyl, lower alkoxy, nitro or trifluoromethyl;
R is lower alkyl;
R' is lower alkyl;
Y is halogen; and
n is 2 or 3;
or a pharmaceutically acceptable salt thereof.

2. A compound represented by the formula:

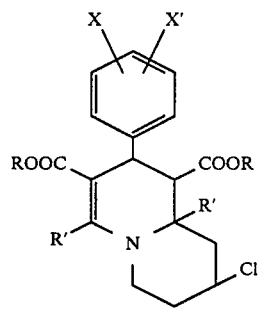

wherein
X are X' are independently hydrogen, halogen, lower alkyl, lower alkoxy, nitro or trifluoromethyl;
R is lower alkyl; and
R' is lower alkyl,
or a pharmaceutically acceptable salt thereof.

3. A compound according to claim 2 wherein R and R' are methyl.

4. A compound according to claim 1 which is dimethyl 8β-chloro-1,6,7,8,9,9a-hexahydro-4,9aα-dimethyl-2-phenyl-2H-quinolizine-1β,3-dicarboxylate.

5. A pharmaceutical composition suitable for treating cardiovascular disorders caused by a high cellular concentration of $Ca^{++}$ comprising at least a therapeutically effective amount of a compound having the formula of a compound of claim 1 in admixture with a pharmaceutically acceptable carrier.

6. A method of treating cardiovascular disorders caused by a high cellular concentration of $Ca^{++}$ which comprises administering to a patient suffering from such disorders a therapeutically effective amount of a compound of claim 1.

7. A process for preparing a compound having the formula:

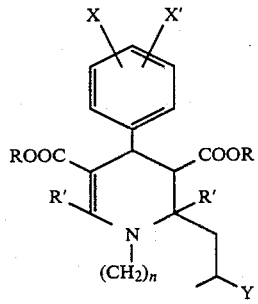

wherein
X and X' are independently hydrogen, halogen, lower alkyl, lower alkoxy, nitro or trifluoromethyl;
R is lower alkyl;
R' is lower alkyl;
Y is halogen; and
n is 2 or 3
which comprises reacting a compound having the formula

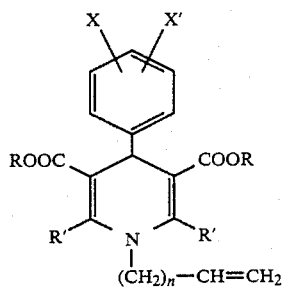

with an acid catalyst in an inert solvent under an inert atmosphere, wherein said acid catalyst is selected from the group consisting of titanium tetrachloride, gaseous hydrogen chloride, gaseous hydrogen bromide, zinc iodide, zinc chloride, boron trifluoride, and aluminum chloride.

* * * * *